Nov. 20, 1934. A. B. CURTIS Plant Pat. 113
RASPBERRY VARIETY
Filed Aug. 12, 1933
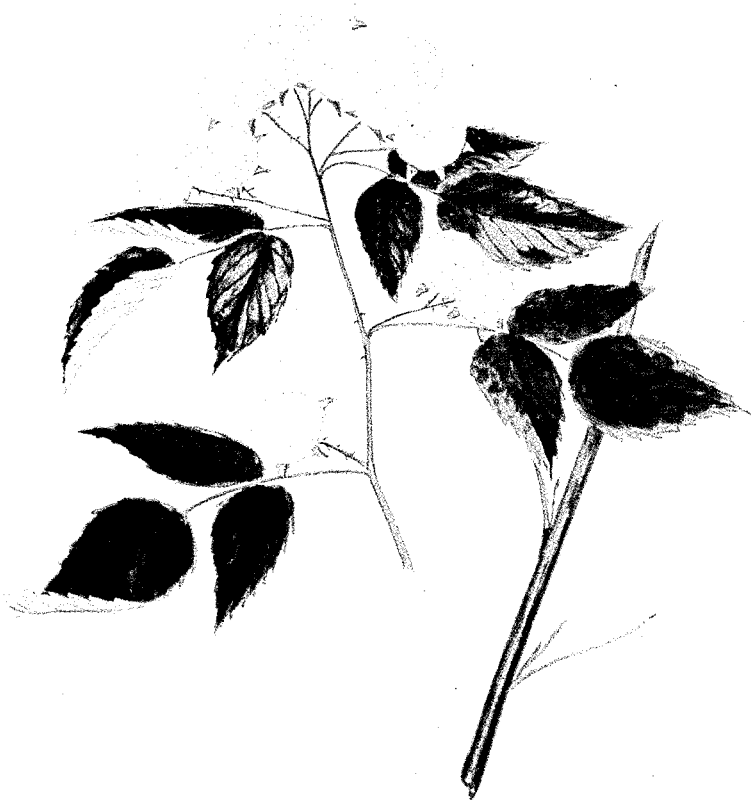
ASAPH B. CURTIS Inventor
By Lester Largent Attorney Patented Nov. 20, 1934

Plant Pat. 113

UNITED STATES PATENT OFFICE

113

RASPBERRY VARIETY

Asaph B. Curtis, Sarona, Wis.

Application August 12, 1933, Serial No. 684,893

1 Claim. (Cl. 47—62)

The object of my invention is the production of a new variety of raspberry plant having a berry of cream color with a light pink hue or cast, and having strong light green canes, free from briars and which propagates in profusion and early in the season.

The fruit and plant are illustrated in the accompanying drawing, which is a perspective view showing a spray of the fruit also showing the color of the leaves, together with a separate portion of the stalk or cane to show its color and freedom from briars.

The bush of this raspberry variety is strong and upright, with a bushy top, is very productive, very vigorous and very healthy and stands drought best of all raspberries; it does not winterkill and requires no protection even at 30 and 40 degrees below zero. It is well adapted to all soils. The plant has very strong, light green or white canes which have few or no briars. The canes are numerous and stocky and adapted well to the bush. The leaves are of a rather light green color, and the back of the leaves are of a very light color green. The flowers on the plant bloom in June and the plant propagates the berries from the tips of the stems like black raspberries. The berries ripen in Wisconsin between July 4th and July 25th. It is a good size berry and bears in profusion. It ripens before other raspberries and therefore brings a good price. The berries, when fully ripe, are of a cream color with a light pink hue, as shown in the accompanying drawing. The berries have a flesh that is juicy. It is of very pleasant taste and the flavor of the fruit is a little different from all other raspberries. It is considered the best berry for canning, preserves and jams. The berries stand shipment well. The berries adhere well to the bush; in fact, the adherence is very strong. The fruit is medium to large and does not crumble.

I have tested the new raspberry plants in various soils and it does well in any soil, and stands drought well.

These raspberry plants have been asexually propagated to the following extent: I found the original plant in the woods and got three small plants from it. I have since asexually reproduced over ten thousand plants and I am making sales in this locality.

What I claim is:

A hardy light colored raspberry plant as shown and described, characterized by very strong light green canes, free from briars, with light green leaves, and able to thrive in any soil and to stand drought well and also characterized by a profusion of cream colored slightly pink berries borne at the ends of stems, the berries having a good flavor and ripening early in the season.

ASAPH B. CURTIS.